Figure 1:
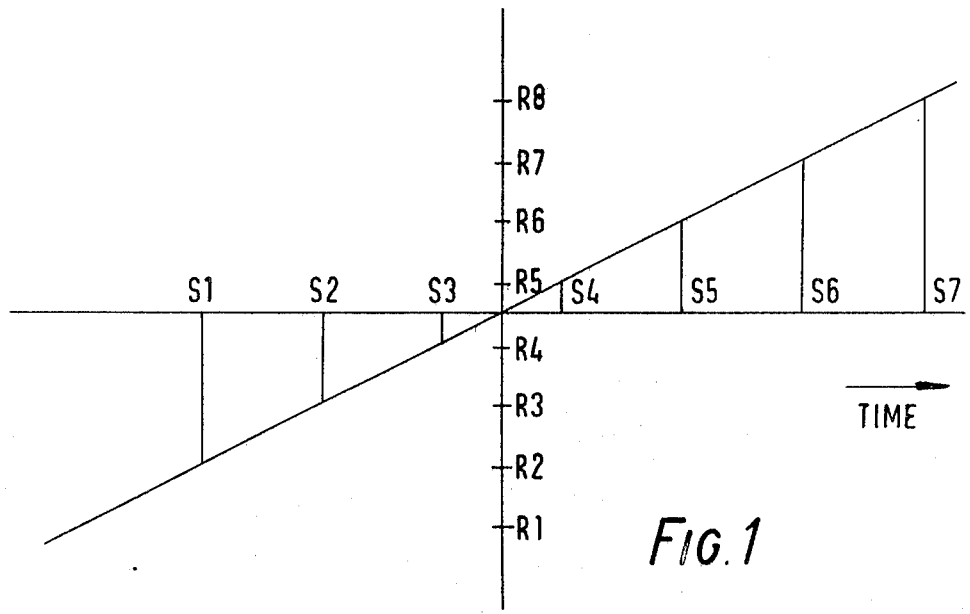

United States Patent [19]
Lodge et al.

[11] 4,086,492
[45] Apr. 25, 1978

[54] DISPLAY APPARATUS FOR USE IN RADIOGRAPHY

[75] Inventors: James Alec Lodge, Maidenhead; John James Jarrett, Chalfont St. Peter, both of England

[73] Assignee: EMI Limited, England

[21] Appl. No.: 757,507

[22] Filed: Jan. 7, 1977

[30] Foreign Application Priority Data

Jan. 21, 1976  United Kingdom .................. 2264/76

[51] Int. Cl.² ............................ A61B 6/02; H05G 1/30
[52] U.S. Cl. ............................ 250/416 TV; 250/445 T
[58] Field of Search .......... 250/363 S, 416 TV, 445 T

[56]   References Cited
U.S. PATENT DOCUMENTS 3,499,146  10/1966  Richards .......................... 250/445 T

*Primary Examiner*—Alfred E. Smith
*Assistant Examiner*—T. N. Grigsby
*Attorney, Agent, or Firm*—Cooper, Dunham, Clark, Griffin & Moran

[57]  ABSTRACT

In computerized diagnostic X-ray apparatus data can be provided for a plurality of parallel sectional representations of the body of a patient. If, however, data are required for planes at different orientations in the body it has been usual to realign the body in relation to the apparatus and repeat the examination. It is now proposed to assemble data for inclined planes through the body by reassembly of data for the sections actually examined. The method of achieving this is described, together with a suitable apparatus for the purpose.

6 Claims, 6 Drawing Figures

DISPLAY APPARATUS FOR USE IN RADIOGRAPHY

The present invention relates to apparatus for processing data for representations of body sections derived from, for example, diagnostic X-ray apparatus for subsequent display.

Apparatus has been described, for example in U.S. Pat. No. 3,778,614, using radiographic techniques to produce representations of the absorption to penetrating radiation of one or more cross-sections of the body of a patient. The absorption is represented by absorption coefficients of individual elements of a matrix of elements notionally delineated in each such cross section.

In U.S. Pat. No. 4,029,948 there is described apparatus for processing and displaying such data which can hold and display individually such representations for a plurality of such cross-sections, typically eight. That apparatus is also capable of interpolating between corresponding matrix elements of adjacent cross-sections to provide data representative of further cross-sections intermediate those actually examined.

U.S. Pat. No. 3,499,146 discloses a laminographic X-ray apparatus which provides X-ray data relating to desired planes of a body. The method and apparatus described there are significantly different from those of the said U.S. Pat. No. 3,778,614. There is however disclosed in the said United States Patent a method of processing data relating to a plurality of examined parallel planes to construct data for other planes orthogonal to those examined. U.S. Pat. No. 3,499,146 indicates generally the procedure to be followed although it does not describe a convenient arrangement for applying them. Furthermore it does not clearly described the production of data for inclined planes through the body although the possibility of obtaining such data is mentioned.

It is an object of the present invention to provide an improved data organisation arrangement capable of convenient production of data for inclined body sections.

According to the invention there is provided a display processing apparatus, for cooperating with X-ray apparatus providing data signals representing the distribution of absorption of the radiation in each of a plurality of substantially parallel spaced planar sections of a body, the data for each section forming a frame of one or more fields of scanned lines; the display processing apparatus including storage means for storing the data signals of each frame, means for deriving from the storage means data signals forming a composite frame, of one or more fields of scanned lines, representing the distribution of the absorption of the radiation in a further planar section intersecting at least some of the first mentioned sections, said composite frame being formed from lines or parts of lines relating to parts of the body in the intersected first mentioned sections and within a predetermined distance of the plane of the further section, and switch control means, responsive to one or both of line or frame frequency sawtooth waveforms, providing switching pulses each suitable for causing the means for deriving to derive data from a different frame in a predetermined sequence.

In order that the invention may be clearly understood and reading carried into effect examples thereof will now be described with reference to the accompanying drawings of which:-

Figure 2:
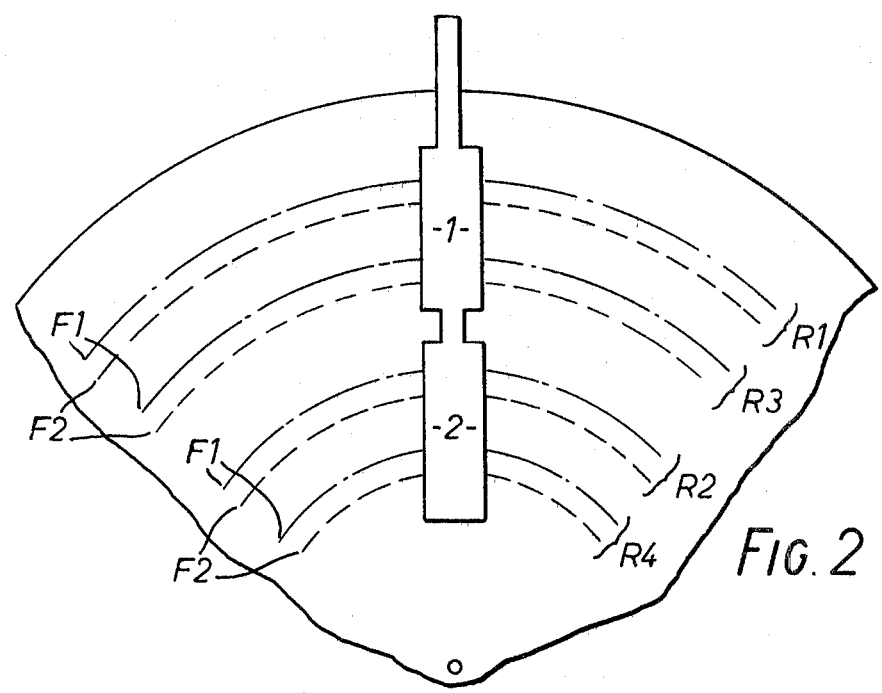
Figure 3:
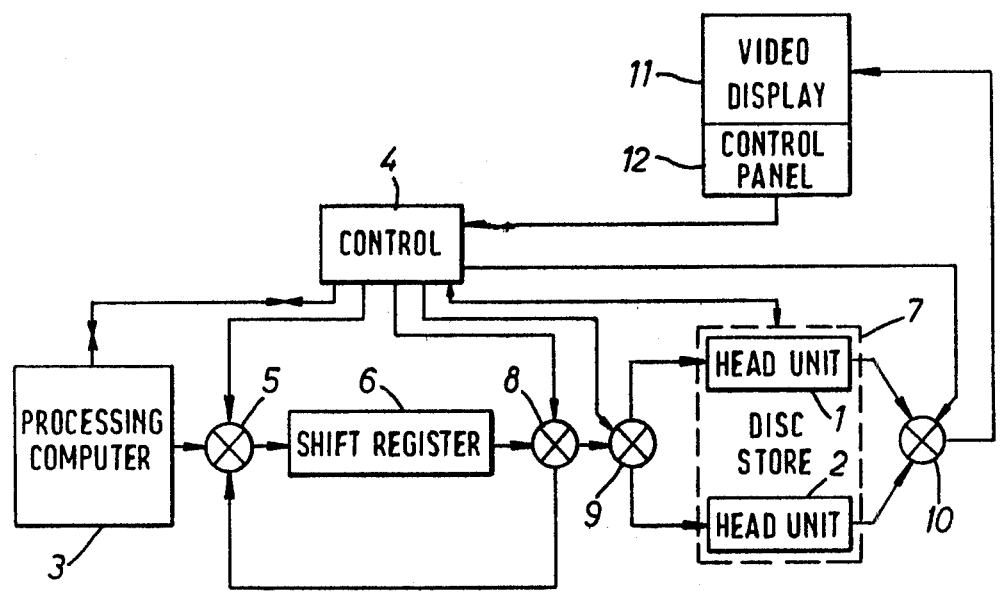
Figure 6:
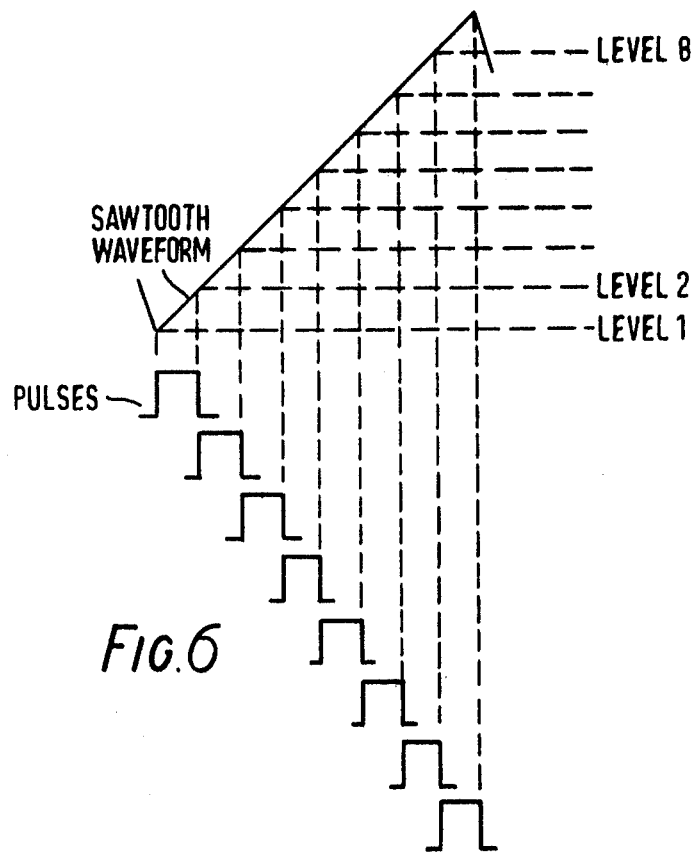
Figure 4:
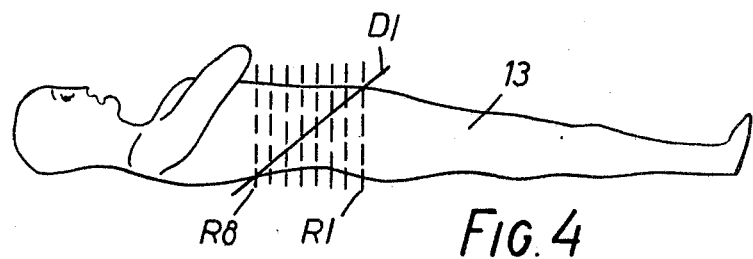
Figure 5:
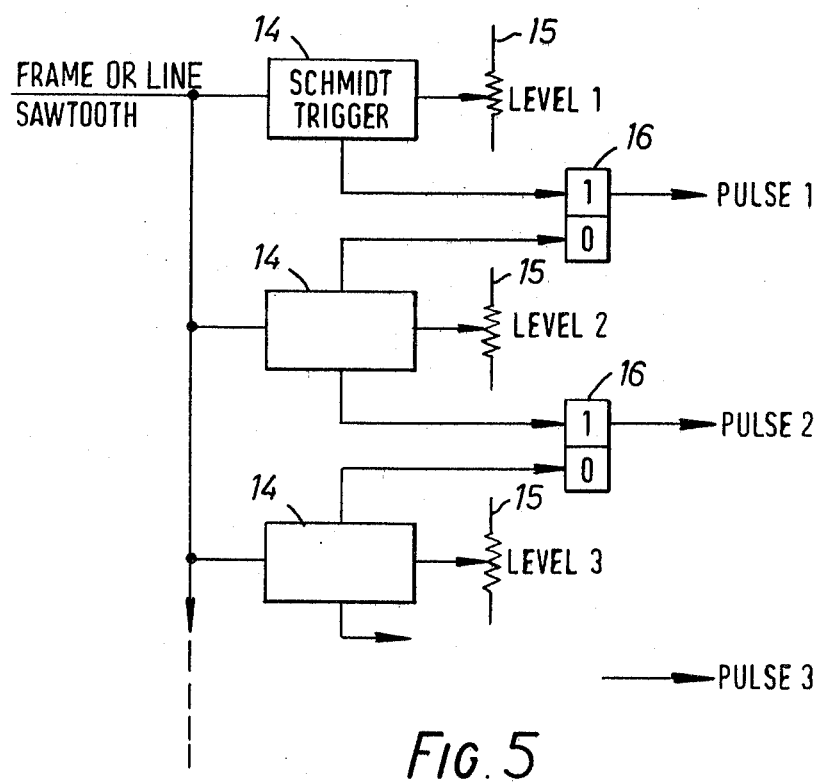

FIG. 1 illustrates a sequence of operation of the invention,

FIG. 2 illustrates the manner of organising data, representing a plurality of spaced cross sections of a body, on a video disc, FIG. 3 shows in block diagrammatic form a circuit for operating the video disc of FIG. 2, FIG. 4 illustrates the disposition of examined cross-sections in a body, FIG. 5 is an example of a circuit suitable for use with the invention and FIG. 6 shows the nature of output pulses provided by the circuit of FIG. 5.

In a typical embodiment the X-ray apparatus, with which the present invention is intended to co-operate, provides a representation, for each derived cross-section of a patient's body, as a television type field of 320 active lines from which a 280 line field for television display may be derived by any suitable means. The representations are also repeated to derive a further field from each, with half line sync shift. The two fields are then combined, in normal interlaced manner, for display.

It will be understood that the cross-sections for which the representations are derived are normally parallel to each other. However it may be desired, for diagnostic purposes or for radiotherapy following diagnosis, to display cross-sections which are not parallel to those derived. In the arrangement of the present invention such cross-sections are synthesised from the already available parallel cross-sections by taking appropriate strips, for example television lines, from each "parallel" representation.

Gating signals for switching between adjacent representations are generated, in this example, by sawtooth waveforms. Two waveforms are provided, of television line and frame frequencies, and the display is switched from one "parallel" representation to another as each sawtooth passes a predetermined threshold level.

The situation is shown in FIG. 1 for one such waveform of voltage increasing with time from left to right. A falling sawtooth may of course be used if desired. Initially the representation being displayed is that labelled R1 but at the point labelled S1 a switch is made to representation R2 as the present threshold is crossed. Other further switches are made, as shown until finally, after the switch labelled S7, representation R8 is being displayed. If the television fields for each representation are being run through simultaneously the switching will represent a change from one to another at corresponding points in the fields. Suitable choice of the sawtooth waveform decides the actual positions on the fields of the changeover points. As mentioned the waveform may be at line or field frequency. Alternatively it may be a suitable combination of these, or may be independently derived.

The pictures derived from the X-ray apparatus are, in one example, stored on two circumferential tracks of a video disc store. Typically the store has thirty two tracks, each with its own recording and reproducing head, in each of two zones which have independent input/output channels. The arrangement of the data on the disc is shown in FIG. 2, on which for clarity only eight tracks are shown, four for each of two recording head units 1 and 2. The tracks relating to the heads of unit 1 are for two representations R1 and R3 and those relating to unit 2 are for intervening representations R2 and R4. In general data for R1, R3, R5 and R7 are stored on one set of tracks and for intervening slices R2, R4, R6 and R8 on the other. The positions of tracks relating to field F1 of each picture are shown by chain dotted lines and those for the other field F2 by dashed lines.

The data are applied to their respective tracks, as will be explained hereinafter, and may be withdrawn as required via either or both of the independent output channels of head unit 1 or head unit 2. It will be appreciated that, since these head units correspond to independent channels and because of the interlaced nature of the track allocations, data for adjacent representations may be withdrawn simultaneously. This is convenient either to allow ready switching between adjacent representations or to allow interpolation between them to provide further representations for cross-sections at intermediate positions in the body. It will be understood that the track being read by either head unit may be changed as desired.

A suitable circuit for use with a disc store of the type described is shown in FIG. 3. The data for each representation is supplied by a processing computer 3, which may be as described in the aforesaid U.S. Pat. No. 3,499,146 or alternatively as described in U.S. Pat. No. 3,924,129, under the control of a control unit 4 which determines the required action in known manner according to input instructions from an operator at a control panel 12. The data appear at the processing computer at a rate incompatible with the television rate and are to be applied to the disc store in units of one line of the picture. The control unit 4 applies the data via a gate 5 to a shift register 6. It will be understood that the parameters of the operation are known in advance by the unit 4 which merely requires information from processing computer 3 to indicate the completion of each line and field of the representation. Unit 4 can therefore be programmed in any suitable manner to initiate the required action in response to predetermined input signals from an operator or the other circuit elements.

As mentioned hereinbefore, the data are applied in units of one line. The data are initially stored in shift register 6 until the disc store, indicated by the broken outline at 7, indicates by a suitable control pulse that the start location of the first stored line, initially the start of the respective field, is available. All complete lines in register 6 are then recorded via gates 8 and 9. Up to eight complete lines can, in this example, be provided by the processing in one revolution of the disc and this is, therefore, the maximum storage required by the shift register 6. Any partial lines stored in shift register 6 when that revolution is completed are discarded and resupplied later by computer 3 for reasons which will become clear. The data from the shift register 6 are applied to the input/output channel of head unit 1 or 2 by gate 9, in response to control pulses from control unit 4, according to the particular representation being generated. This is according to the scheme outlined in relation to FIG. 2. This disc store 7 is instructed to apply the data to the track of field F1 for that picture. At the same time gate 8, in response to control pulses from control unit 4, recirculates these lines to register 6 via gate 5 from which they are again applied to the disc store at the corresponding locations of field F2 of the same picture. On the second passage they are not recirculated by gate 8 and the computer 3 is instructed to recommence supplying data at the start of the next complete line. This data is in turn recorded when the location for the start of that line is available and the cycle repeated until the two identical fields of one entire picture are recorded. It will be understood that, if desired, only one of these fields need be recorded and the other could be generated, with appropriate delays, immediately before display.

This sequence is repeated for the picture of each of a series of constructed representations of absorption until each is in store. It will be noted that the thirty two tracks of the disc store of this example can hold sixteen such pictures. This facility is used to store a second eight pictures of the same representations. These are, however, modified by the computer 3 according to various parameters, such as for example the application of a "window" of maximum and minimum levels, in response to operator controls 12 after viewing the original pictures.

For display a picture may be provided by the disc store and applied via gate circuit 10 to a standard television display 11. Display 11, which may be a conventional video monitor is situated together with the operator's control panel 12. Circuit 10 is arranged to pass a single picture on either of its inputs from head units 1 and 2 or to combine two outputs provided by those units simultaneously to provide data for interpolated representations as desired.

The arrangement described in relation to FIGS. 2 and 3 is substantially the same as that disclosed and claimed in U.S. Pat. No. 4,029,948. That application also describes a suitable circuit for the gate circuit, shown at 10 in FIG. 3, to allow the provision of representations at positions intermediate to the measured cross-sections. It should be understood in relation to the present invention that the 'parallel' representations, from which diagonal representations are to be derived, may in practice include such interpolated representations.

The present invention is intended to provide data for representations which may be termed 'diagonal' since they relate to cross sections in the body which are not in planes parallel to those actually examined by the X-ray apparatus. To achieve this the derivation of data from disc store 7 commences from the track holding the data for one representation and switches in sequence, and in the course of one field, to tracks for other representations. The orientation of the 'diagonal' representation depends, of course, on the rate and timing of that switching. It will also be apparent that a better approximation to a true 'diagonal' representation is obtained if interpolated representations are used.

For better understanding of the invention the operation will be described first in terms of a diagonal slice which is merely inclined from the vertical. It is assumed that eight cross sections were examined for a patient lying horizontally on his back. Each cross section is then vertical and top to bottom represents front to back of the patient. The sequence of cross sections thus take positions which are horizontally displaced. This is illustrated in FIG. 4 in which a body 13 is intersected by cross sections for the representations R1 to R8, shown as broken lines. The desired diagonal cross-section is indicated by D1 in solid line and is also in a plane perpendicular to the paper.

It will be apparent that, if the display of the cross-sections is such that the front of the patient is at the top of the picture, the 'diagonal' representation D1 can be provided by the topmost lines of R1 and progressively lower lines from R2, R3 . . . R8. For this purpose head unit 1 reads from track 1 of the disc, i.e. field F1 of representation R1, for one eighth of the total field time, head 2 from field F1 of R2 for the second eighth, and head 1 from field F1 of R3 for the third eighth. This continues until a first field has been built up from F1 for all representations and then continues with F2 fields for all representations in the same manner before being repeated.

The switching from one track to another is in this example in response to a respective one of a sequence of eight pulses provided by a series of Schmidt triggers from a frame frequency sawtooth waveform.

A suitable arrangement is shown in FIG. 5. The frame sawtooth is supplied to a plurality of Schmidt triggers 14, one for each level at which a change of track is required. Each Schmidt trigger 14 cooperates with a respective potentiometer 15 from which the desired level is set. The outputs of the Schmidt triggers are provided in pairs to bistable circuits 16 such that each trigger circuit 14 provides a pulse when its level is exceeded and simultaneously terminates the pulse of the preceding trigger circuit. The sequence of pulses provided by this circuit is shown in FIG. 6. The pulses are supplied to control unit 4 which causes head units 1 or 2 and gate circuit 10 to supply the appropriate data.

If the 'diagonal' is required to be obtained from less than the full eight representations the amplitude of the frame frequency sawtooth can be altered accordingly or alternatively the level control potentiometers can be adjusted. The sawtooth may also be D.C. shifted to alter the relative position of the 'diagonal' representation. As noted hereinbefore, the sawtooth waveform may be of opposite polarity in which case the 'diagonal' representation would be oppositely disposed.

For very shallow diagonals, close to the horizontal, the number of lines in the frame may be much reduced compared with the vertical picture. In the extreme of a horizontal slice there are, in the absence of interpolation, only eight independent lines in such a frame. Even using a typical degree of interpolation fifteen lines is a probable figure. However even such restricted frames at a desired inclination offer useful information for diagnostic purposes.

It will be understood that, if interpolated representations are used, more than eight levels may be required.

For other dispositions of the 'diagonal' representation a similar technique is applied. For example, if the 'diagonal' is to be level from front-to-back of the patient but tilted from right to left, a line frequency sawtooth waveform is substituted. In this case the output pulses are used to switch the heads 1 and 2 through each track of the relevant field in succession in the course of each line. Other considerations are as described hereinbefore.

For slanting 'diagonal' representations, tilted from front-to-back and from left to right both frame and line sawtooth waveforms are required with two pulse circuits such as that of FIG. 5. The output pulses of these two circuits are then combined in an analogue AND gate to change tracks along each line as in the side-to-side case but providing also a relative displacement of the tracks chosen as the position in the frame changes.

In a practical arrangement in which circuit timing is provided by, for example, a 4MH$_z$ clock, the track selection pulses may be provided by suitable digital processing of the clock pulses.

What we claim is:

1. A display processing apparatus, for cooperating with X-ray apparatus providing data signals representing the distribution of absorption of x-radiation in each of a plurality of substantially parallel spaced planar sections of a body, the data signals for each section forming a frame of one or more fields of scanned lines; the display processing apparatus including storage means for storing the data signals of each frame, means for deriving from the storage means data signals forming a composite frame, of one or more fields of scanned lines, representing the distribution of the absorption of the radiation in a further planar section intersecting at least some of the first mentioned sections, said composite frame being formed from lines or parts of lines relating to parts of the body in the intersected first mentioned sections and within a predetermined distance of the plane of the further section, a source of one or both of line or frame frequency saw-tooth waveforms and switch control means, responsive to said one or both of line or frame frequency sawtooth waveforms, providing switching pulses each suitable for causing the means for deriving to derive data from a different frame or line in a predetermined sequence.

2. A display processing apparatus according to claim 1 in which the switch control means is responsive to a frame frequency sawtooth waveform to cause the means for deriving to derive one or more lines of each of the frames of intersected sections in sequence.

3. A display processing apparatus according to claim 1 in which the switch control means is responsive to a line frequency sawtooth waveform to cause the means for deriving to assemble each line of the composite frame from parts of the corresponding lines of the frames of the intersected sections.

4. A display processing apparatus according to claim 1 in which the switch control means includes at least one sequence of threshold means each of which is arranged to provide an output signal when a respective level of one of said sawtooth waveforms is exceeded.

5. A display processing apparatus according to claim 4 including bistable circuits cooperating with said threshold means to cause the output signal from one threshold means to cancel the output signal of an adjacent threshold means having a lower threshold level.

6. A display processing apparatus according to claim 4 in which the threshold means are Schmidt triggers.

* * * * *